United States Patent [19]
Windhagen et al.

[11] Patent Number: 6,017,341
[45] Date of Patent: Jan. 25, 2000

[54] APPARATUS FOR FIXATION OF THE BONES IN A HEALING BONE FRACTURE

[75] Inventors: Henning J. Windhagen, Hannover; Michael J. Raschke, Berlin, both of Germany

[73] Assignee: Novo Nordisk A/S, Bagsvaerd, Denmark

[21] Appl. No.: 09/218,568

[22] Filed: Dec. 22, 1998

Related U.S. Application Data

[63] Continuation of application No. PCT/DK97/00271, Jun. 20, 1997.

[51] Int. Cl.[7] .................................................. A61B 17/62
[52] U.S. Cl. ............................................ 606/56; 606/102
[58] Field of Search ................................ 606/53, 54, 55, 606/56, 57, 58, 59, 102; 600/595

[56] References Cited

U.S. PATENT DOCUMENTS 4,576,158  3/1986  Boland .

FOREIGN PATENT DOCUMENTS

| | | |
|---|---|---|
| 0 324 279 | 7/1989 | European Pat. Off. . |
| 3305597 | 8/1984 | Germany . |
| 4113083 | 10/1992 | Germany . |
| WO 96/34585 | 11/1996 | Switzerland . |
| 2 031 731 | 4/1980 | United Kingdom . |

*Primary Examiner*—Michael Buiz
*Assistant Examiner*—David O. Reip
*Attorney, Agent, or Firm*—Steve T. Zelson, Esq.

[57] ABSTRACT

The present invention relates to methods for measuring the strength of a healing bone fracture by rotating the bones about their axis at each side of the fracture relative to each other and measure the needed rotational moment as a function of the rotational angle obtained. The present invention also relates to apparatus comprising a first (5) and a second (8) ring shaped member, studs (15) connecting these members (5, 8) with an axial distance from each other, and fixing pins (6, 14) rigidly connecting the respective ring shaped members and the bone (1) at respective sides of the fracture. One ring member (8) comprises a first (10) and a second (9) element joined so that they can be rotated but not axially displaced relative to each other, the first element (10) carrying the studs (15) and the second element (9) carrying the fixing pins (14). The elements (9, 10) forming the second ring member (8) are engaged by respective jaws of a tong shaped tool provided with measuring devices (42, 47) to measure the length of the movement of the jaws and the force needed for this movement.

5 Claims, 3 Drawing Sheets

APPARATUS FOR FIXATION OF THE BONES IN A HEALING BONE FRACTURE

CROSS-REFERENCE TO RELATED APPLICATIONS

This application is a continuation application of PCT/DK97/00271 filed Jun. 20, 1997 and claims priority under 35 U.S.C. 119 of Danish application 0705/96 filed Jun. 27, 1996, the contents of which are fully incorporated herein by reference.

BACKGROUND OF THE INVENTION

The invention relates to devices for fixation of the bone ends at each side of a fracture.

It is known that the healing of bone fractures may be controlled when the bone ends at each side of the fracture is fixated adjacent to each other. Even if a part of the bone is missing the ends of the bones may during the healing be drawn slowly apart and the increased space between the bone ends will then be filled up with new bone mass.

It is important that the bone is not substantially loaded until the healing process has developed sufficiently to carry the load and consequently a method and an apparatus enabling a measuring of the healing status of the bone without loading it excessively is wished for. However the strength of the healed bone may only be measured by loading the bone moderately and measuring its response to the load.

U.S. Pat. No. 5,339,533 describes a system for measuring the stiffness of a healing fractured bone. By this system the fixation device is dismounted and replaced by a bending stress goniometer. With one end of the fractured bone resting on a load cell the fractured part is pressed until a bending of 0,5–1° is obtained and the load on the load cell is recorded. After the measuring the fixation rod is remounted unless the measuring shows that the bone has obtained sufficient strength so that further treatment can be stopped. A repetitive dismounting and remounting of the fixture means risk of dislocation of the bone ends when they are not supported by an external fixture and during the remounting.

From EP 0 117 859 a method for indirectly measuring the strength of a healing bone is described. This is obtained by equipping a clamping bar connecting pins fixed in the bone ends at each side of the fracture with strain gauge measuring strips by which it may continuously be measured which load is carried by the external fixture. By this method the external fixture is not removed and it may be estimated to which extent a load is carried by the fixture, but an explicit value reflecting the strength of the healing bone is not obtained.

EP-A-0324279 describes an apparatus for measuring fracture stiffness. The apparatus comprises a goniometer which is positionable to run substantially parallel to the long axis of the bone having the fracture and which has one end connected with a first spacer, placed axially to one side of the fracture, and the other end connected with a second spacer place axially to the other side of the fracture, and said apparatus including means to measure the signal of the goniometer to obtain a measurement of angular deformation on the application of a load, said measurement being representative of fracture stiffness. By this apparatus the bending of the bone is measured as a function of the load applied. Care is taken to avoid errors due to rotation at the fracture.

SUMMARY OF THE INVENTION

It is an object of the invention to provide a method by which drawbacks by the known methods are overcome.

This is obtained by a method for measuring the strength of a healing bone which method is characterised in that the ends of the bones at each side of the fracture are fixed to respective external holders by which they are rotated relative to each other mainly about the axis of the bone and the rotational moment necessary to perform said rotation is measured as a function or the angle of rotation.

Further it is an object to provide an apparatus by which the bone ends at each side of the fracture can be rotated relative to each other but at the same time can be maintained in their axial position relative to each other so that axial loads are carried by the apparatus.

This is obtained by an apparatus for fixation of bone ends at each side of a fracture, which apparatus according to the invention is characterised in that it comprises a first and a second ring member, each forming at least a part of a circular ring, studs connecting the ring shaped members keeping them in axial distance from each other and along which at least one of the ring members can be displaced axially and clamped in a chosen distance from the other ring, fixing pins extending radially inwards from each of the two ring shaped members to establish a rigid connection between the respective ring members and the bone at the respective sides of the fracture, wherein one of the ring members is a two-piece member composed of a first and a second ring elements which are joined together so that they can be rotated but not axially displaced relative to each other, the first ring element carrying the studs and the second ring element carrying the fixing pins, and fixing means being provided by which the first and the second ring elements can be fixed to each other to clamp them against mutual rotation.

DETAILED DESCRIPTION OF THE INVENTION

Figure 1:
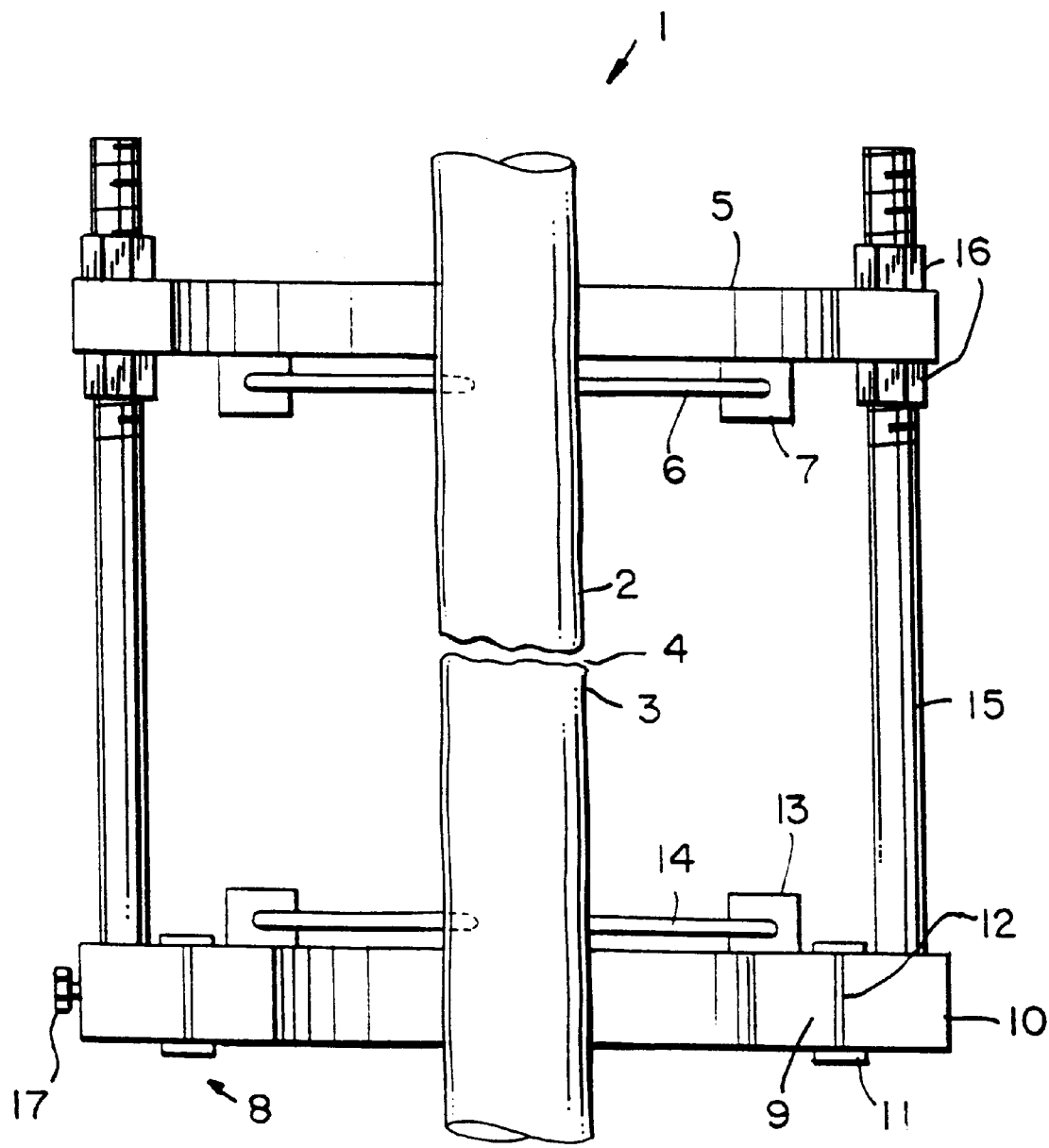

By this apparatus a fixation of the bone ends on each side of the fracture may be obtained and at the same time the apparatus allows measuring of the strength of the healing bone using the method according to the invention without dismounting the fixator apparatus. Only the clamping together of the two ring elements of the two-piece ring members have to be released to allow rotation of the second ring element, which carries fixing pins fixing the bone at one side of the fracture to this second ring element, relative to the first ring element which through studs is rigidly fixed to the one-piece ring member which is again through pins rigidly fixed to the bone end on the other side of the fracture.

The ring members may be shaped as only parts of a rings. This makes it easier to mount the ring members as the limb with the broken bone do not have to be inserted through the ring but may be passed sideways into the ring to be positioned in the center thereof.

The studs keeping the ring members in a distance from each other may according to the invention be threaded and the one-piece ring member may be clamped between nuts on the studs. This allows use of the apparatus for drawing the bone ends away from each other during the healing if necessary as the one-piece ring element may be displaced along the studs by turning the nuts clamping this element.

The elements forming the two-piece ring member are provided with means by which jaws of a tong shaped tool may be fastened to the respective elements. The tong shaped tool may be used to rotate the two ring elements and consequently the bone ends directly or indirectly fixed to these two elements in relation to each other.

The tool may be provided with a measuring device by which the length of the movement of the jaws and thereby the rotational angle of the relative rotation of the two bone ends may be measured. Another measuring device in the tool measures the force which was needed to provoke the measured rotation. The length measuring device may according to the invention be a potentiometer mounted rigidly connected to one jaw of the tong and having its slider mechanically connected to the other jaw. Thereby the resistance measured between the electric connections to one end of the potentiometer and to its slider will be proportional with the distance the jaws are moved relative to the other. A load cell provided between one of the handles of the tool and the jaw operated by this handle may provide a signal reflecting the force used to move the jaws relative to each other. On the basis of the signals from the potentiometer and from the load cell an appropriately programmed computer may calculate and show the rotational angle obtained as a function of the rotational moment exerted on the bone ends.

According to the invention an electric motor may be mounted on one of the ring elements and be driving the other ring element when activated. Further force measuring means may be provided measuring the torque by which the motor rotates the other ring, and angle measuring means may be provided measuring the angle of the relative movement of the two ring elements, and stops may be provided to stop the relative movement if either the torque or the angle exceeds set values. By these features the apparatus is applicable for subjecting healing bones to frequent loads within set limits during the healing process. Such micromotion has shown to be good for the fracture healing at a certain time of the healing process A control circuit may be provided which on basis of pre-set values and feed-back signals from the measuring means controls the motor to affect a fractured bone fixed by the fixator according to the invention with rotational loads according to a pre-set load pattern. At the same time as the loads are applied on the bone, corresponding values of torque and rotation angle are automatically measured to reflect the effectiveness of the therapy.

Figure 2:
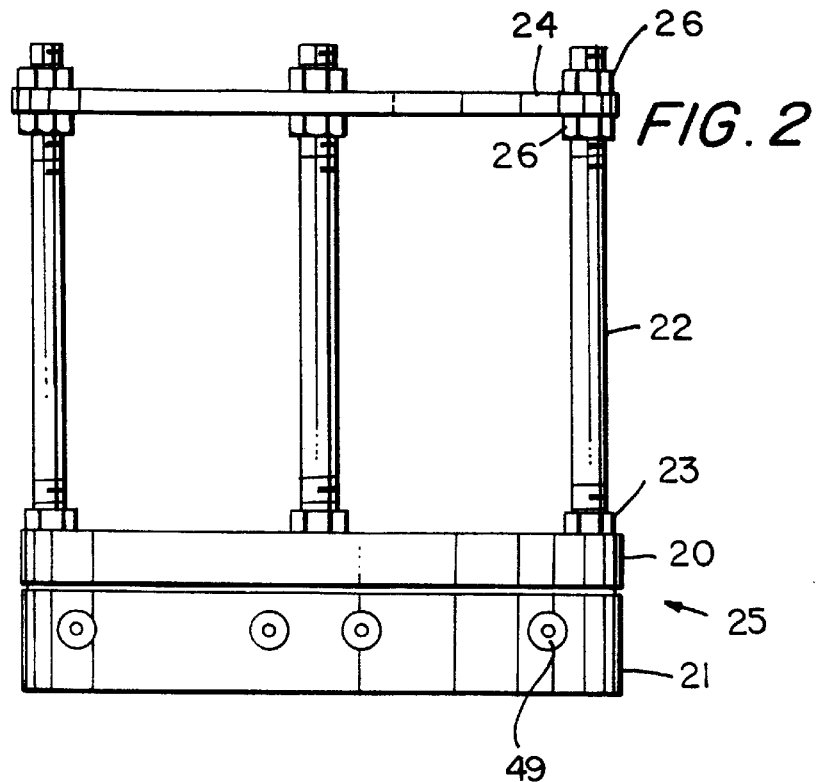
Figure 3:
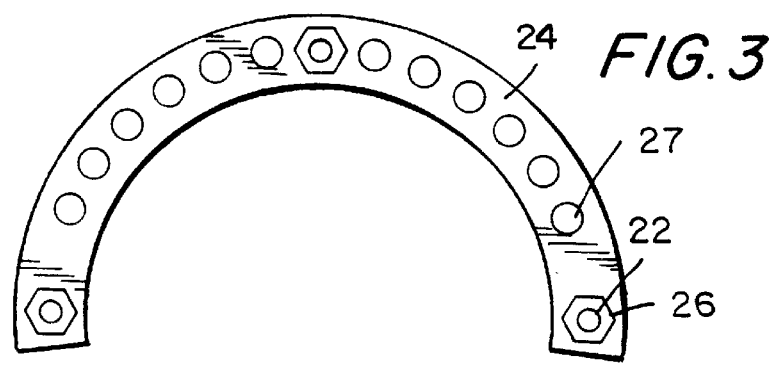
Figure 4:
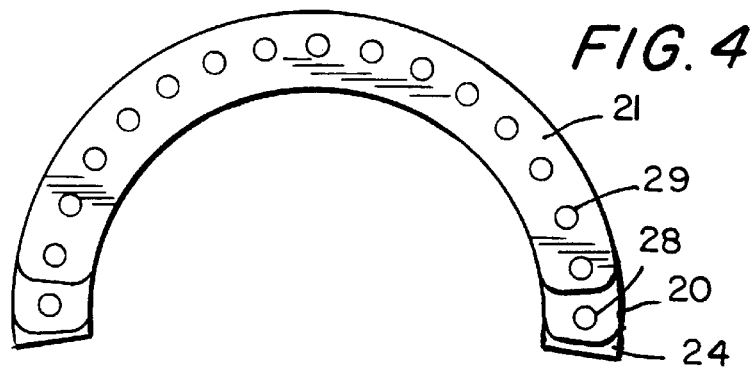

In the following the invention is described in further details with references made to the drawing, wherein FIG. 1 shows schematically a fixator according to the invention mounted on a broken bone, FIG. 2 shows an embodiment of the fixator according to the invention, FIG. 3 shows a top view of the fixator in FIG. 2, FIG. 4 shows a bottom view of the fixator in FIG. 2

Figure 5:
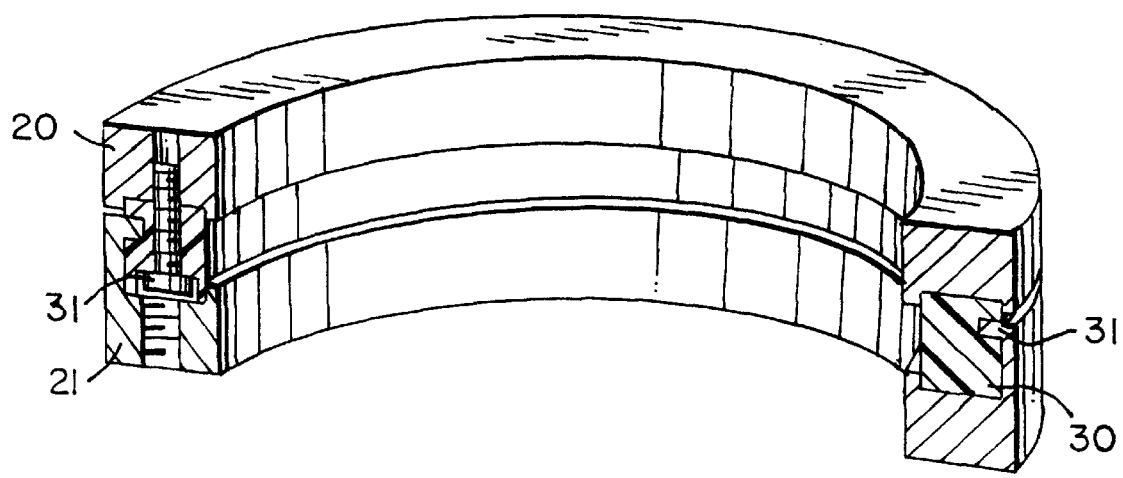
Figure 6:
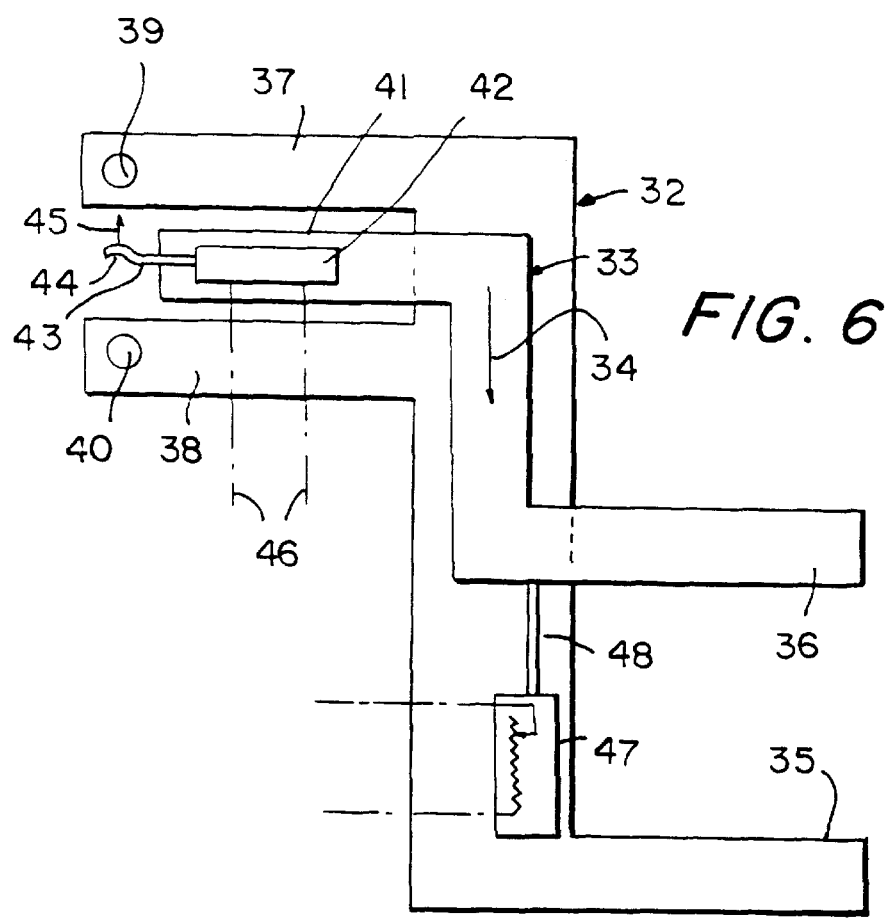

FIG. 5 shows schematically in perspective the second ring of the fixator shown in FIG. 2, FIG. 6 shows schematically a tool for rotating the adjacent ends of a broken bone on each side of a fracture relative to each other and for providing electronic signals reflecting relevant parameters of said rotation.

In FIG. 1 is a broken bone 1 has a first and a second end, 2 and 3 respectively, on respective sides of the fracture which forms a gap 4 between the two ends. The first end 2 of the bone is fixed to a first ring member 5 by pins 6 which are mounted in brackets 7 on the ring member 5 and are anchored in the bone end 2.

A second ring member 8 is composed of an inner and an outer ring element, 9 and 10 respectively. The inner ring element 9 has an outer diameter corresponding to the inner diameter of the outer ring element 10 so that the inner ring element 9 forms a journal for the outer ring element 10. Stop rings 11 mounted on one of the ring elements cover the circular gap 12 between the two elements prevents axial movement of the ring elements relative to each other. The gap 12 may just be wide enough to form a running fit between the two ring elements 9 and 10.

Brackets 13 mounted on the inner ring element 9 carry pins 14 which are anchored near the second end 3 of the broken bone to fix this end to said inner ring element. The outer ring element 10 carries a number of studs 15 which are mounted perpendicularly to the plane defined by said outer ring element. The first ring member 5 is mounted on the studs 15 at a distance from the second ring member 8 mainly parallel with said second ring member. The first ring element is mounted between two nuts 16 which are screwed onto the studs 15 which are at least at their free ends provided with a thread. By this mounting the bone is placed mainly through the centres of the ring elements 5 and 8 and is running parallel with the studs. The distance between the two ring members 5 and 8 may easily be changed if this is wanted, e.g. to pull the bone ends adjacent to the fracture away from each other.

When the ring elements 9 and 10 of the second ring member 8 are clamped together by tightening a screw 17, the apparatus serves as a fixator maintaining the two bone ends 2 and 3 in a chosen position relative to each other. When it is wanted to measure the obtained strength of the healing fracture this may be obtained without dismount in the fixator only the screw 17 must be loosened to allow relative rotational movement of the two ring elements 9 and 10. By this rotational movement the part of the bone comprising the fracture will be the object of a torque which may be measured and set in relation to the rotational angle of the rotation causing said torque.

The two ring elements of a second ring member 25 may be placed beneath each other as shown in FIG. 2. An upper ring element 20 is rotatably mounted on a lower ring element 21. Threaded studs 22 are screwed into the upper ring element 20 and is secured by lock nuts 23. In a distance from the second ring member a first ring member 24 is fastened between sets of nuts 26 on the studs 22 passing through holes in said first ring member.

FIG. 3 shows the apparatus in FIG. 2 seen from above and shows that the first ring member forms about a half circle and is provided with angular spaced holes 27. The studs 22 are passed through some of these holes whereas other holes are free to accommodate brackets for holding pins by which the first ring member may be anchored to the bone end at one side of a bone fracture.

FIG. 4 shows the apparatus in FIG. 2 seen from the bottom. Here it is seen that the upper and the lower ring elements forms about half a circle. The upper ring element 20 projects a little over the ends of the lower ring element 21. Both ring elements are provided with holes. The threaded studs 22 may be screwed into some of the holes 28 in the upper ring element 20. Some of the holes 29 in the lower ring element 21 may be used for mounting of brackets carrying pins which anchors the lower ring element to the bone end at the other side of the fracture. Other of the holes in the two ring elements may be used for mounting a measuring tool as it shall be described below.

As shown in FIG. 5, which in perspective shows the second ring member 25 in the apparatus shown in FIG. 2, a sliding journal for the lower ring element 21 is formed by a ring 30 of a low friction material clamped to the upper ring element 20 by bolts with heads 31 which are countersunk in the low friction material not to interfere with the sliding of the lower ring 21 on the provided journal. The ring 30 is provided with a circumferential groove which is engaged by a circumferential flange 31 on the lower ring element to allow relative rotational but not relative axial movements of the two ring elements. Relative rotational movement of the two ring elements may be prevented by clamping the two ring elements together by screwing screws 49 in the lower ring as shown in FIG. 2 to engage the ring 30.

FIG. 6 shows schematically a tool which may be used with the fixator to rotate the two adjacent bone ends of a fractured bone relative to each other and to measure the angle of rotation and the torque exerted on the bone to obtain said rotation. The tool comprises a basis 32 and a slider 33 which may be displaced relative to the basis in the direction indicated by an arrow 34. The basis 32 and the slider 33 are each provided with grips, 35 and 36 respectively, which may be gripped by a hand and moved towards each other to provide said relative displacement. The base is provided with two arm 37 and 38 each provided with a hole 39 and 40, respectively. Instead of the two arms, one broad arm with two holes may be provided. The holes 39 and 40 are provided with a spacing allowing the basis to be fixed to the lower ring by bolts through said holes screwed into a pair of the holes 29 in the lower ring element 21. This way the basis 32 is made non rotatable relative to this lower ring element and the second ring element 25 as a whole.

The slider is provided with an arm 41 parallel with the arms 37 and 38 of the basis. The arm 41 carries a force transducer 42 having an measuring arm 43 with a hook 44 lying in line with the two holes 39 an 40. The transducer 42 provides an electric signal reflecting a force exerted in the direction of the arrow 45 at the hook 44 on the measuring arm 43. The electric signal from the transducer 42 is through electric leads 46 lead to a computer. The slider arm 41 with the transducer 42 is elevated over the basis so that the hook 44 of the transducer lies above the upper ring element 20 when the basis is fastened with its arms 37 and 38 abutting the lower side of the lower ring element 21. The tool may be so positioned that the hook 44 can grip on one of the threaded studs 28 carried by the upper ring element 20. Alternatively a pin may be inserted in one of the holes 28 in the upper ring element to form a point of application for a rotating force exerted on the upper ring element 20 through the hook 44 when the grips 35 and 36 of the tool is moved towards each other.

The distance the grips 35 and 36 is moved towards each other is measured and transformed into an electric signal by a displacement transducer 47 fixed to the basis 32 and having an actuator arm 48 connected to the slider 33. In the figure it is suggested how such a displacement transducer may be formed by a linear potentiometer having its resistor fixed to one of the parts and its slider fixed to the other of the parts the relative movement of which is going to be measured. However, the displacement transducer may be of any appropriate kind and the shown suggestion shall not form any limitation of the invention. Electric signals from the displacement transducer 47 are lead to the computer and the torque exerted on the bone is calculated as a function of the rotational displacement which has caused it.

During the measurements the two ring elements 20 and 21 of the second ring member are released to be rotatable relative to each other. When the measuring is finished the two ring elements are again clamped to each other to form a rigid second ring elements. When care is taken to move the two ring elements back into their original rotational position relative to each other before they are clamped together when the measuring sequence is finished, it is further ensured that the position of the two bone ends at each side of the fracture is held in their original position relative to each other.

The tool is described in an embodiment designed for use with the embodiment of the fixator shown in FIG. 2 but may of course be modified to be used with other embodiments.

If connected values for measured angles and torques are plotted against each other a curve will be obtained from which the bone stiffness will be reflected by the slope of the curve. However, a number of sources of errors may influence the curve and must be compensated for. E.. the pins by which the bone ends are fixed to the ring members, may show some play in their anchoring in the bone. This will give a curve having one slope as long as the rotation only takes up the play and another slope when the bone is actually twisted. It also must be remembered that the torque causes a twisting not only of the bone but also of the fixator itself. Consequently the fixator rigidity has to be excluded for accurate measurements. This may be done by initially measuring the fixator stiffness at a range of loads and store the connected values for torque and the angle the fixator is twisted by this torque where after a controlling software may automatically correct measured data for the twisting of the fixator.

Numerous studies have shown that controlled loading of a healing bone results in increased bone formation. Magnitude of forces, frequency of application and duration of such loads are currently under scientific evaluation. Whatever combination of loading pattern is most suitable can be exerted on the fracture by the use of the fixator according to the invention. The loading being a rotational loading may be exerted through the fixator apparatus when the ring elements of the second ring is released to rotate relative to each other and an electric motor fastened to one ring element and is driving the other ring. The applied torque may be reflected by the power consumption of the motor or by force transducers between the ring and the motor base. The application of forces and moments may be controlled through a closed loop controlling in accordance with the healing of the fracture.

We claim:

1. An apparatus for measuring the strength of a healing bone fracture by measuring the force needed for relative rotation of the ends of the bones at each side of the fracture as a function of the rotational angle obtained which apparatus has means for fixation of the bone ends (2 and 3) at each side of a fracture, comprising, a first (5; 24) and a second (9,10; 25) ring shaped member forming at least a part of a ring studs (15; 22) connecting the ring shaped members (5;24 and 9,10; 25) keeping them in axial distance from each other and along which at least one (5;24) of the ring shaped members can be displaced axially and clamped in a chosen distance from the other ring (9,10; 25), and fixing pins (6,14) extending radially inwards from each of the two ring shaped members to establish a rigid connection between the respective ring shaped members and the bone (1) at the respective sides of the fracture, wherein one (9,10; 25) of the ring members is composed by a first (10; 20) and a second (9; 21) ring elements which are joined together so that they can be rotated but not axially displaced relative to each other, the first element (10; 20) carrying the studs (15; 22) and the second element (9; 21) carrying the fixing pins, and a measuring tool coupled to the first and second ring member (5,9,10; 20,21) to rotate these ring members relative to each other and measure the rotation angle and the torque exerted to perform said rotation.

2. An apparatus of claim 1, wherein the fixing means (49) are provided by which the first and the second ring elements (20, 21) can be fixed to each other to clamp them against mutual rotation.

3. An apparatus of claim 1, wherein the elements (20, 21) forming the second ring member (25) each are provided with means which can be engaged by the jaws (37, 38 and 44) of a tong shaped tool forming the measuring tool.

4. An apparatus of claim 3, wherein the tong shaped tool is provided with measuring devices (47, 42) measuring the length of the movement of the jaws (37, 38 and 44) of the tong and the force needed for this movement.

5. An apparatus of claim 4, wherein the measuring devices are a slide resistance (47) and a load cell (42), respectively, by which electric signals representing distance and force can be provided.

* * * * *